United States Patent [19]

Hayes et al.

[11] Patent Number: 5,599,290
[45] Date of Patent: Feb. 4, 1997

[54] BONE FRACTURE PREVENTION GARMENT AND METHOD

[75] Inventors: Wilson C. Hayes, Lincoln; Stephen N. Robinovitch, Belmont; Thomas A. McMahon, Wellesley, all of Mass.

[73] Assignees: Beth Israel Hospital, Boston; President and Fellows of Harvard College, Cambridge, both of Mass.

[21] Appl. No.: 979,154

[22] Filed: Nov. 20, 1992

[51] Int. Cl.⁶ .......................... A61F 13/00; A41D 13/00
[52] U.S. Cl. .................. 602/61; 602/23; 2/455; 2/465
[58] Field of Search .................. 2/2; 602/61, 62, 602/26, 27, 23, 5, 60; 128/882

[56] References Cited

U.S. PATENT DOCUMENTS

| | | | |
|---|---|---|---|
| D. 334,063 | 3/1993 | DeWall | D24/190 |
| D. 341,981 | 12/1993 | Harris | D6/601 |
| 729,293 | 5/1903 | Dorman . | |
| 1,165,669 | 12/1915 | Hedgcock . | |
| 1,229,947 | 6/1917 | Haggerty . | |
| 1,468,072 | 9/1923 | Ogle . | |
| 1,740,171 | 12/1929 | Goldsmith . | |
| 1,756,358 | 4/1930 | Ingram . | |
| 1,774,739 | 9/1930 | Voyne . | |
| 1,786,268 | 12/1930 | Snavely . | |
| 2,247,961 | 7/1941 | Mulvey | 2/2 |
| 2,481,291 | 9/1949 | Coleman | 2/43 |
| 2,607,934 | 8/1952 | Bailhe | 9/20 |
| 2,663,020 | 12/1953 | Cushman | 2/2 |
| 2,745,106 | 5/1956 | Salhus | 2/215 |
| 2,851,390 | 9/1958 | Chavannes | 154/125 |
| 2,889,830 | 6/1959 | Raymond | 128/522 |
| 2,917,051 | 12/1959 | White | 128/522 |
| 2,934,766 | 5/1960 | Cherup | 2/2 |
| 2,935,130 | 5/1960 | Moore | 166/44 |
| 3,026,874 | 3/1962 | Stevens | 128/260 |
| 3,044,075 | 7/1962 | Rawlings | 2/22 |
| 3,185,362 | 5/1965 | Wakefield | 224/9 |
| 3,304,938 | 2/1967 | Perkins, Jr. | 128/132 |
| 3,322,873 | 5/1967 | Hitchcock | 264/222 |
| 3,334,626 | 8/1967 | Schimmel | 128/154 |

(List continued on next page.)

FOREIGN PATENT DOCUMENTS

| | | |
|---|---|---|
| 0099010 | 1/1984 | European Pat. Off. . |
| 0153082 | 8/1985 | European Pat. Off. . |
| 0351147 | 1/1990 | European Pat. Off. . |
| 8603019 | 4/1986 | Germany . |
| 3937648C1 | 5/1991 | Germany . |
| 1002955 | 9/1965 | United Kingdom . |
| 2082919 | 3/1982 | United Kingdom . |
| WO86/03655 | 7/1986 | WIPO . |
| 9101658 | 2/1991 | WIPO ............... 2/2 |
| 9311678 | 6/1993 | WIPO . |
| WO93/15701 | 8/1993 | WIPO . |

OTHER PUBLICATIONS

"As Nation Grows Older, Falls Become Greater Source of Fear, Injury, Death", Jody W. Zylke, M.D., *Medical News & Perspectives*, JAMA, Apr. 18, 1990, vol. 263, No. 15, p. 2021.

"Research Focuses Not Only on Where, Why, How of Falls, but Also on Preventing Them", Jody W. Zylke, M.D., *Medical News & Perspectives*, JAMA, Apr. 18, 1990, vol. 263, No. 15, p. 2022.

*Primary Examiner*—Richard J. Apley
*Assistant Examiner*—Beverly M. Flanagan
*Attorney, Agent, or Firm*—Bromberg & Sunstein

[57] ABSTRACT

A garment, in one embodiment of the invention, reduces the risk of bone fracture of a human or animal subject due to impact forces on a vulnerable region having a bone part near the skin surface when the vulnerable region is proximate to a soft tissue region lacking a bone part near the skin surface. The garment has an arrangement for shunting a substantial portion of the impact energy from the vulnerable region to the soft tissue region, where such energy may be safely absorbed and/or dissipated. In a further embodiment, there is utilized a dilatent material that is relatively stiff near the time of impact and relatively fluid at other times. Related methods are also provided.

40 Claims, 15 Drawing Sheets

U.S. PATENT DOCUMENTS

| | | | |
|---|---|---|---|
| 3,435,946 | 4/1969 | Sobek et al. | 206/46 |
| 3,438,377 | 4/1969 | Connors | 128/528 |
| 3,446,880 | 5/1969 | Enicks | 264/45 |
| 3,526,221 | 9/1970 | Garber | 128/95 |
| 3,528,416 | 9/1970 | Chamberlain | 128/154 |
| 3,550,159 | 12/1970 | Alarco | 2/2 |
| 3,552,044 | 1/1971 | Wiele | 36/71 |
| 3,577,305 | 5/1971 | Hines et al. | 161/4 |
| 3,596,972 | 8/1971 | Pool | 294/103 |
| 3,601,923 | 8/1971 | Rosenberg | 46/151 |
| 3,609,764 | 10/1971 | Morgan | 2/3 |
| 3,663,447 | 5/1972 | Murphy | 252/136 |
| 3,713,640 | 1/1973 | Margan | 267/117 |
| 3,771,170 | 11/1973 | Leon | 2/2 |
| 3,783,879 | 1/1974 | Stalder | 128/570 |
| 3,806,950 | 4/1974 | Spencer-Foote | 2/3 |
| 3,848,802 | 11/1974 | Degginger et al. | 239/10 |
| 3,872,511 | 3/1975 | Nichols | 2/3 |
| 3,921,222 | 11/1975 | Hollman | 2/2 |
| 3,990,440 | 11/1976 | Gaylord, Jr. | 128/149 |
| 3,991,423 | 11/1976 | Jones | 2/415 |
| 4,000,737 | 1/1977 | Horn | 128/154 |
| 4,023,569 | 5/1977 | Warnecke et al. | 128/154 |
| 4,067,063 | 1/1978 | Ettinger | 2/2 |
| 4,116,236 | 9/1978 | Albert | 128/80 |
| 4,134,399 | 1/1979 | Halderson | 128/132 |
| 4,142,252 | 3/1979 | Storer | 2/24 |
| 4,151,613 | 5/1979 | Rhee | 2/2 |
| 4,185,327 | 1/1980 | Markve | 2/2 |
| 4,213,202 | 7/1980 | Larry | 2/2 |
| 4,219,892 | 9/1980 | Rigdon | 2/24 |
| 4,250,882 | 2/1981 | Adair | 128/275 |
| 4,292,263 | 9/1981 | Hanrahan et al. | 264/46.9 |
| 4,308,010 | 12/1981 | De Woskin | 433/5 |
| 4,338,926 | 7/1982 | Kummer et al. | 128/92 |
| 4,346,525 | 8/1982 | Larsen et al. | 36/69 |
| 4,360,012 | 11/1982 | McHarrie et al. | 128/92 |
| 4,367,748 | 1/1983 | Masso Remiro | 128/521 |
| 4,370,754 | 2/1983 | Donzis | 2/2 |
| 4,371,636 | 2/1983 | Distler et al. | 523/223 |
| 4,390,995 | 7/1983 | Walck | 2/9 |
| 4,399,816 | 8/1983 | Spangler | 128/154 |
| 4,471,538 | 9/1984 | Pomerantz et al. | 36/28 |
| 4,472,839 | 9/1984 | Johansen | 2/338 |
| 4,491,656 | 1/1985 | Serini et al. | 528/167 |
| 4,518,335 | 5/1985 | Pujari | 425/78 |
| 4,536,539 | 8/1985 | Lundberg et al. | 524/521 |
| 4,538,301 | 9/1985 | Sawatzki et al. | 2/2 |
| 4,547,919 | 10/1985 | Wang | 5/455 |
| 4,573,216 | 3/1966 | Wortberg | 2/2 |
| 4,584,339 | 4/1986 | Lundberg et al. | 524/516 |
| 4,602,384 | 7/1986 | Schneider | 2/2 |
| 4,607,629 | 8/1986 | Lerman | 128/80 |
| 4,633,863 | 1/1987 | Filips et al. | 128/165 |
| 4,641,641 | 2/1987 | Strock | 2/2 X |
| 4,654,396 | 3/1987 | Bung et al. | 524/401 |
| 4,700,403 | 10/1987 | Vacanti | 2/2 |
| 4,737,994 | 4/1988 | Galton | 2/2 |
| 4,761,834 | 8/1988 | Kolb | 2/2 |
| 4,807,301 | 2/1989 | Ferber | 2/2 |
| 4,821,431 | 4/1989 | Rieffel | 36/88 |
| 4,884,295 | 12/1989 | Cox | 2/2 |
| 4,892,551 | 1/1990 | Haber | 623/23 |
| 4,905,681 | 3/1990 | Glascock | 128/155 |
| 4,907,576 | 3/1990 | Curlee | 128/78 |
| 4,913,755 | 4/1990 | Grim | 156/145 |
| 4,917,112 | 4/1990 | Kalt | 128/156 |
| 4,926,503 | 5/1990 | Wingo, Jr. | 2/2 X |
| 4,926,883 | 5/1990 | Strock | 128/888 |
| 4,951,656 | 8/1990 | Gorka et al. | 128/90 |
| 4,985,931 | 1/1991 | Wingo, Jr. | 2/2 |
| 5,027,801 | 7/1991 | Grim | 602/27 X |
| 5,034,998 | 7/1991 | Kolsky | 2/2 |
| 5,037,880 | 8/1991 | Schmidt et al. | 524/823 |
| 5,054,121 | 10/1991 | Mitchell | 2/2 |
| 5,057,111 | 10/1991 | Park | 606/69 |
| 5,062,433 | 11/1991 | Kummer | 128/888 |
| 5,066,296 | 11/1991 | Chapman et al. | 606/64 |
| 5,070,865 | 12/1991 | Iams | 128/78 |
| 5,077,849 | 1/1992 | Farley | 5/464 |
| 5,094,238 | 3/1992 | Gibbon | 128/403 |
| 5,098,124 | 3/1992 | Breed et al. | 280/751 |
| 5,098,421 | 3/1992 | Zook | 604/367 |
| 5,100,189 | 3/1992 | Futamata et al. | 293/132 |
| 5,105,473 | 4/1992 | Valtakari | 2/2 |
| 5,111,542 | 5/1992 | Farley | 5/464 |
| 5,117,969 | 6/1992 | Roth | 198/807 |
| 5,122,146 | 6/1992 | Chapman et al. | 606/102 |
| 5,123,407 | 6/1992 | Dewhurst | 602/2 |
| 5,138,722 | 8/1992 | Urella et al. | 2/209 |
| 5,139,240 | 8/1992 | Miyamoto et al. | 267/140 |
| 5,150,767 | 9/1992 | Miller | 182/137 |
| 5,157,789 | 10/1992 | Klass | 2/114 |
| 5,161,257 | 11/1992 | Arensdorf et al. | 2/2 |
| 5,165,296 | 11/1992 | Abbas et al. | 5/612 |
| 5,178,811 | 1/1993 | Farley | 264/113 |
| 5,179,792 | 1/1993 | Brantingham | 36/29 |
| 5,184,409 | 2/1993 | Brown | 36/44 |
| 5,191,659 | 3/1993 | Backus | 2/227 |
| 5,191,752 | 3/1993 | Murphy | 54/44.5 |
| 5,230,947 | 7/1993 | Ou | 428/212 |
| 5,246,654 | 9/1993 | Ertle et al. | 264/118 |
| 5,252,373 | 10/1993 | Ganske et al. | 428/68 |
| 5,257,418 | 11/1993 | Jaskiewicz | 2/20 |
| 5,277,697 | 1/1994 | France et al. | 602/16 |
| 5,284,468 | 2/1994 | Nelson | 602/5 |

BONE FRACTURE PREVENTION GARMENT AND METHOD

This invention was supported under NIH Grant No. AR40321, and the U.S. Government has certain rights to the invention.

TECHNICAL FIELD

The present invention relates generally to garments for bone fracture prevention, especially for the prevention of hip fracture during impact from a fall, and related methods.

BACKGROUND ART

Hip Fracture Epidemiology

Fractures of the proximal femur are a major source of mortality and morbidity among the elderly. Approximately 250,000 hip fractures occur in the United States annually. Nearly 33 percent of women and more than 17 percent of men will experience a hip fracture if they live to age 90. Among patients who are functionally independent prior to a hip fracture, 15 to 25 percent remain in long-term care settings for more than a year afterward. Another 25 to 35 percent are dependent on others for their mobility. More than half of those that survive hip fracture never recover normal function. Moreover, the average mortality associated with hip fracture in elderly patients is approximately 20 percent in the first year.

The public health impact of hip fractures is also staggering. Recent surveys in the United Kingdom have shown that at any one time about 50 percent of acute orthopedic beds are occupied by hip fracture patients. In the U.S., the average length of hospital stay for hip fracture patient is three weeks, longer than for any other diagnosis. The annual costs associated with the acute and chronic care of hip fracture patients in the United States is estimated to exceed $7 billion. The problem can only be expected to worsen with projected increases in the average age of the world population, leading some to suggest the possibility of a nearly three-fold rise in the total number of hip fractures by the middle of the next century.

Over 90 percent of all hip fractures are caused by falls. However, the majority of falls in the elderly result in only minor injury, with one to three percent causing hip fracture. Surveys among elderly fallers have shown the following factors increase the risk for suffering a hip fracture in a fall (in order of importance): 1) impacting on the hip or side of the leg (which increases the risk of fracture by over 20-fold), 2) having a tall, slender body habitus, 3) falling with a high initial potential energy (which depends on both body mass and the height of the fall), and finally 4) possessing low bone density in the proximal femur. These results suggest the risk for hip fracture in a fall is dominated by the severity of the fall as opposed to the density and strength of the proximal femur. To reduce the incidence of hip fractures, hip fracture prevention strategies must therefore either reduce the incidence of falls, or protect the femur in the event of a fall. The former strategy may be accomplished by restricting mobility, although this carries associated medical risks and impairs personal autonomy and quality of life. It might also be accomplished through exercise programs in the elderly populations at greatest risk for falling, although no study to date has proven the effectiveness of such an approach. In any case, it seems unrealistic to expect the complete elimination of falls among the elderly, given the often multiple factors (cardiac, neural, musculoskeletal) and random causes of falls. It therefore appears that the most reliable method for reducing hip fracture incidence is to protect the femur during the impact stage of the fall. This essentially requires lowering the impact force applied to the femur to a value below its fracture threshold.

Hip fracture refers to fracture of the proximal end of the femur, which is the strongest, heaviest, and longest bone in the body, accounting for approximately one-fourth of total body height. The proximal end of the femur consists of a head, neck, and greater and lesser trochanters. The neck of the femur connects the spherical head to the shaft. It is limited laterally by the greater trochanter, a large, somewhat rectangular lateral projection from the neck and shaft, which provides an insertion site for several muscles of the gluteus region. The greater trochanter lies laterally, just beneath a relatively thin layer of skin and adipose tissue (fat), and can be easily palpated on the lateral side of the thigh. Since it is the most lateral point of the hip region, the greater trochanter is the site which comes into contact with a hard surface when one lies on one's side, and the site where the majority of impact force is applied when one falls sideways onto the hip. Consequently, falls to the side resulting in impact to the greater trochanter carry a high risk for hip fracture.

In contrast to the minimal amount of soft tissue covering the greater trochanter, a considerable quantity of soft tissue exists in the posterior gluteal (buttock) and anterior thigh regions adjacent to the greater trochanter. Upon impact to these regions, this soft tissue is able to absorb significant energy, and lower the impact forces applied to the underlying skeletal structures. Gluteal soft tissues include the gluteus maximus, medius, and minimus muscles, as well as the considerable layer of fat overlying the buttock. The most significant anterior thigh soft tissues are the quadriceps muscles, which include the three vastus muscles and the rectus femoris muscle.

Experimentally, when the elderly cadaveric femur is loaded in a configuration simulating a fall on the hip, the average force required to fracture it is 2040N [Lotz JC and Hayes WC, J Bone Joint Surg [Am], 72-A:689–700, 1990]. The corresponding average energy absorbed by the bone up to fracture is 25 J. At standing height, the potential energy of the body can be well over 20 times this amount. Furthermore, we have conducted experiments which suggest the force applied to the femur at impact from an average sideways fall to the hip is about 6 kN, over three times the mean fracture force (Robinovitch, SN, Hayes, WC, McMahon, TA, J Biomech Eng, 113: 366–374, 1991). It therefore appears that to avoid hip fracture during a fall, one or more of the following must occur: 1) direct impact to the lateral aspect of the hip must be avoided, 2) the impact site must extend outside the hip region, or 3) significant energy must be absorbed by alternative mechanisms such as contraction of the thigh muscles during descent, breaking the fall with an outstretched hand, or deformation of both the floor and the soft tissue overlying the impact sight.

Similar to hip fracture, fracture of other bones such as the tibia, radius, and ulna occurs when the force applied to the bone exceeds that required to initiate fracture. Often such a situation arises when the impact energy is high, and contact occurs to a small area directly overlying the fracturing bony structure. In such circumstances, the impact energy cannot be absorbed and/or dissipated through a large area, and high local stresses are applied to the underlying bone.

Prior Art Protective Devices

Several protective garments have been developed with the aim of preventing hip fractures. All of these devices attempt to reduce fracture incidence by reducing the impact force applied to the femur during a fall on the hip. Most incorporate an energy absorbing and/or dissipating material or structure placed directly over the greater trochanter and surrounding area (Ferber, U.S. Pat. No. 4,807,301; Galton, U.S. Pat. No. 4,737,994; Kolb, U.S. Pat. No. 4,761,834; Kolsky, U.S. Pat. No. 5,034,998; Wortberg, U.S. Pat. No. 4,573,216). The major drawback of such devices is they cover the greater trochanter and proximal femoral diaphysis, and thus transmit load to these regions during impact to the hip. As described previously, these regions of the femur, and in particular the greater trochanter, extend furthest laterally of all bony components of the hip region, and are protected by a minimum of overlying soft tissue. They thus represent the regions of lowest compliance within the total protected area, and subsequently, during impact to the protective garment, the majority of impact force is transmitted to the femur.

A further problem with protective devices which cover the greater trochanter is the compromise that designers face between device thickness and device rigidity. Device thickness largely determines wearer acceptability. The more slender the device, the more acceptable to the wearer. Device rigidity also affects wearer acceptability, since a soft, compliant device is more comfortable to the wearer than a hard, inflexible device. However, device rigidity also determines the amount of energy absorbed and magnitude of force produced by deformation of the device. A very compliant material, while generating low stress or pressure during compression, will also absorb little energy during deformation. Unless a device formed of such a material is several inches thick (and thus unacceptably thick to the wearer), the potential energy available in the fall will overwhelm the energy absorbing capacity of the material, causing it to completely compress or "bottom" before a significant portion of the energy of the fall is absorbed. In this bottomed state, the pad is unable to absorb further energy and the remaining energy must be absorbed by the soft tissues and the bone. To avoid bottoming of the pad under the high impact energies associated with falling, designers have selected relatively stiff elastic or viscoelastic pad materials. For example, U.S. Pat. No. 4,807,301 specifies the use of a viscoelastic foam called Sportcell selected to "not to bottom under the falling stress of normal body weight from a height of two feet". U.S. Pat. No. 4,737,994 describes a device for covering the hip region with an inflated air cushion which, if constructed to not bottom during impact, would become highly pressurized and stiff. Finally, U.S. Pat. No. 4,573,216 describes a fairly stiff silicon rubber pad designed to be worn over the greater trochanter. Such pad materials will absorb significant energy during deformation (or in the case of the inflatable pad, compression of the gas), allowing for a slender design. However, such deformation generates significant stresses or pressures in the pad material, resulting in high forces being transmitted to the underlying femur, and in particular the greater trochanter, which contains a minimal degree of overlying soft tissue.

A second approach taken by inventors of hip fracture prevention devices, is to incorporate a rigid dome-shaped shield into the padding system (Strock, U.S. Pat. Nos. 4,641,641 and 4,926,883; Kummer, U.S. Pat. No. 5,062,433). In Strock's U.S. Pat. Nos. 4,641,641 and 4,926,883, this shield is designed to be centered over the greater trochanter, and upon impact, transfer force away from this region. However, several design features prevent this device from significantly lowering the impact force applied to the femur during a fall. First, only a small amount of force is required to initiate contact between the skin-side surface of the shield and the skin overlying the proximal diaphysis of the femur. Further compression of the pad will result in significant load transfer to the proximal diaphysis, which represents the least compliant portion of the contact region. Second, the small contact area formed between the edges of the rigid shield and the underlying skin favors the generation of high contact stresses, particularly over the relatively stiff proximal femoral diaphysis region which is just distal to the greater trochanter. No evidence exists supporting the notion that higher force is required to fracture the femur when this force is applied to the proximal diaphysis as opposed to the greater trochanter. Indeed, the increased moment arm of this force with respect to the femoral neck may result in femoral fracture at a lower magnitude of applied force.

Other problems with the Strock system, or any system incorporating a rigid shield, include its inability to conform to changes in body shape under normal activities, thus restricting body motion and causing discomfort to the wearer. Furthermore, no method is provided for affixing the Strock pad to the body other than through the use of an adhesive to the skin, making these pads inappropriate for persons who would suffer skin problems due to long-term lack of ventilation to the skin.

SUMMARY OF THE INVENTION

The present invention overcomes many of the disadvantages of the prior art designs by providing, in one embodiment, a garment, for reducing the risk of bone fracture of a human or animal subject due to impact forces on a vulnerable region having a bone part near the skin surface when the vulnerable region is proximate to a soft tissue region lacking a bone part near the skin surface. In this embodiment, the garment has an arrangement for shunting a substantial portion of the impact energy from the vulnerable region to the soft tissue region, where such energy may be safely absorbed and/or dissipated. The embodiment also permits removably mounting the energy shunting arrangement on the subject. In a further embodiment, the energy shunting arrangement includes a component shaped to overlie the soft tissue region but not the vulnerable region, for receiving the impact energy which would otherwise be transmitted to the vulnerable region and retransmitting a substantial portion of this energy to the soft tissue region. This component is mounted so as to overlie the soft tissue region but not the vulnerable region. In yet a further embodiment, the component includes a dilatant material that is relatively stiff near the time of impact and relatively fluid at other times. In a preferred embodiment, the invention provides a hip pad, possessing a thickness small enough to be compatible with wearer acceptability, that conforms to the shape of the body during everyday activities such a walking, sitting, and sleeping, and is thus comfortable to the wearer. Related methods are also provided.

BRIEF DESCRIPTION OF THE DRAWINGS

The features and advantages of the present invention will be better understood by reference to the following detailed description, taken with the accompanying drawings in which.

DETAILED DESCRIPTION OF SPECIFIC EMBODIMENTS

The protective device in accordance with a preferred embodiment of the present invention comprises a horseshoe-shaped garment placed over the hip region so as to contact the skin adjacent, but not overlying, the greater trochanter and proximal diaphysis of the femur. In one embodiment, the garment has one or more envelopes made of a flexible material and containing within a substance which exhibits a marked increase in viscosity with increasing rate of shear deformation. This behavior, which causes the device to exhibit significantly greater flexibility and compliance at low rates of deformation, such as those occurring during everyday activities such as sitting and walking, than during the high rates of deformation surrounding impact, is known as "shear-thickening" or "dilatancy". The relatively flexibility under everyday activity provides a degree of comfort to the wearer far exceeding previous designs which utilize a rigid dome-shaped shield or a relatively inflexible polymeric sheet. The ability of the pad to stiffen upon impact, combined with the horseshoe shape, allows for transmission of the energy of the body on impact into the soft tissues surrounding, but not overlying, the greater trochanter and proximal femoral diaphysis. Due to their bulk, these tissues are capable of absorbing and dissipating the impact energy without the production of large stresses. Since no part of the pad overlies the femur, force transmission to the femur is minimized, occurring at appreciable extent only after compression of the surrounding soft tissues causes the external surface of the pad to be in line with the external surface of the greater trochanter. However, the pad is constructed with a thickness sufficient to ensure this occurs, if at all, only in the most severe falls.

Several possible mechanisms exist for affixing the garment over the hip regions. In one embodiment the protective device is fitted bilaterally into short pants, either in the form of cloth underwear or well fitted flexible shorts similar in appearance and function to those worn by bicyclists. In another embodiment, the protective device employs cloth straps which wrap around both the waist and thigh regions on the wearer, and possess a hook-and-pile fastener material such as that sold under the VELCRO trademark, to permit adjusting the position of the device to achieve optimal placement on the wearer. In another embodiment, the protective device is affixed to the hip regions of the wearer through the use of adhesive strips on the inner surface of the device permitting it to secured to the skin in the optimal position over the hip region.

It is believed that the invention provides an arrangement that is more effective at reducing the force applied to the femur during impact on the hip from a fall and more comfortable to wear than prior art pads.

Figure 1:
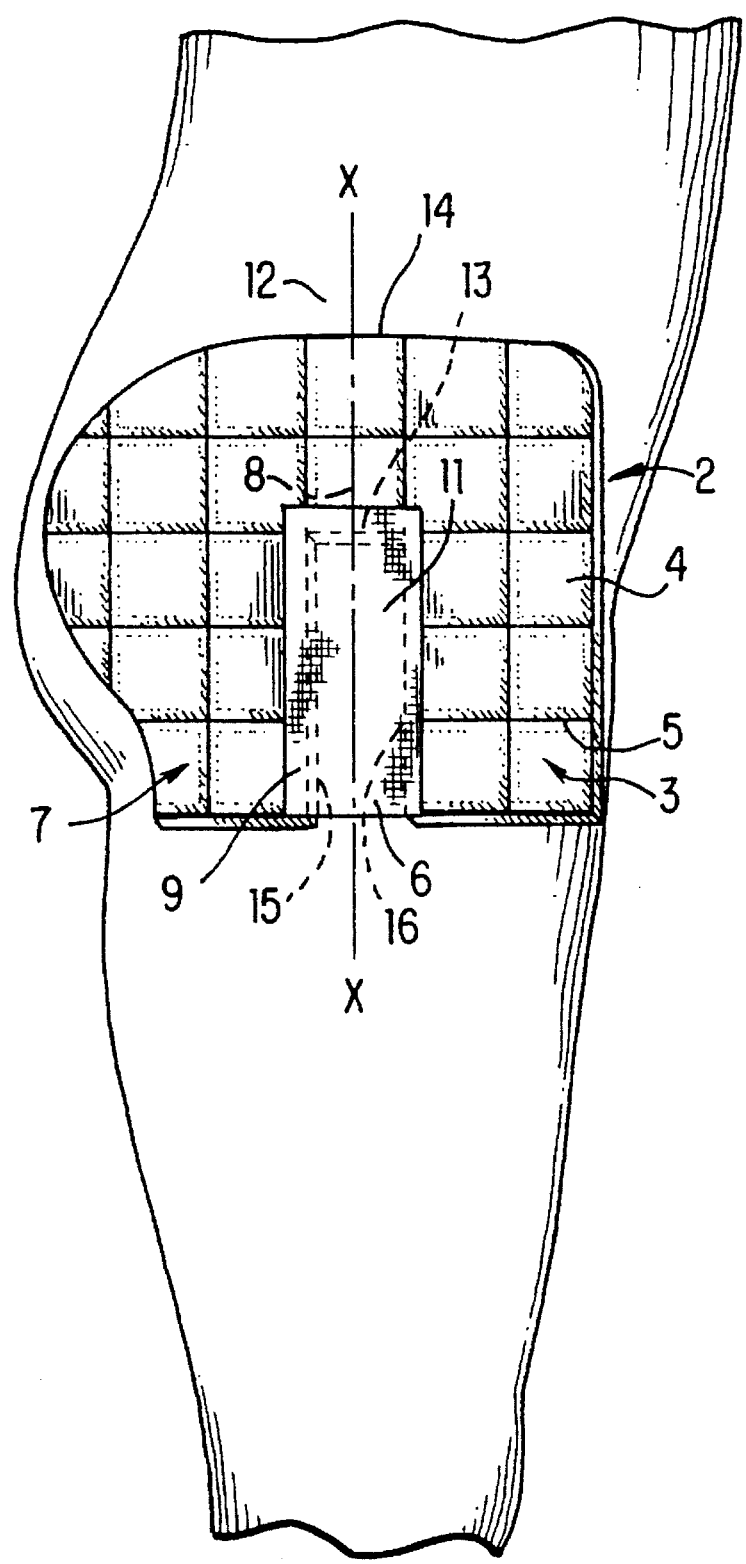
FIG. 1 is a perspective view of a protective garment in accordance with the present invention shown as worn on the hip of a human subject.

FIG. 1 shows a perspective view of a protective garment embodied in accordance with the present invention and worn on the hip of a human subject. The garment 2 has a number of flexible and compliant envelopes 4 each containing a shear-thickening or dilatant material. The compliant envelopes 4 are separated by bonds, and are arranged to form an inverted "U" or horseshoe shape approximately centered about the midpoint 8 of the greater trochanter of the femur. The anterior portion of the device 3 is connected to the posterior portion of the device 7 a flexible but relatively non-compliant strip 6, which may be made of cloth. This cloth 6 is secured to the compliant envelopes on the superior internal border of the horseshoe 13, the anterior internal border of the horseshoe 16, and the posterior internal border of the horseshoe 15 by means of a bond 9.

In the embodiment of the invention illustrated in FIG. 1, the horizontal distance between the posterior internal border of the horseshoe 15 and the anterior internal border of the horseshoe 16 is relatively constant over the length of the pad at a value of approximately 40 mm. However, alternative embodiments may exist involving devices where this width is constant at a value between 30 and 70 mm, or devices involving variations in this width along the length of the pad between 30 and 70 mm. The device is so positioned that, along a horizontal line 8 passing through the greater trochanter, the posterior internal border of the horseshoe 15 and the anterior internal border of the horseshoe 16 are roughly an equal horizontal distance from the midpoint 8 of the greater trochanter. Similarly, along any horizontal line below the greater trochanter midpoint 8 and passing through the protective garment 2 and the axis 10 of the proximal femoral diaphysis, the anterior internal border of the horseshoe 16 and the posterior internal border of the horseshoe 15 are roughly an equal horizontal distance from the axis X—X of the proximal femoral diaphysis.

Again referring to FIG. 1, the superior internal border of the horseshoe 13 is located roughly 20 mm above the midpoint of the greater trochanter of the femur 8. However, alternative embodiments of the device may exist where the location of the superior internal border of the horseshoe 13 is constant at a value between 10–40 mm above the midpoint of the greater trochanter 8. Further alternative embodiments may exist where the location of the superior internal border of the horseshoe 13 varies between 10–40 mm above the midpoint of the greater trochanter.

In the embodiment of the invention shown in FIG. 1, the external border of the device 14 extends inferiorly to approximately 10 cm below the midpoint of the greater trochanter, posteriorly (at its greatest extent) to approximately 10 cm horizontal to the greater trochanter midpoint 8, superiorly to approximately 2 cm below the location 12 of the superior iliac spine, and anteriorly to approximately 7 cm horizontal to the greater trochanter midpoint.

Figure 2:
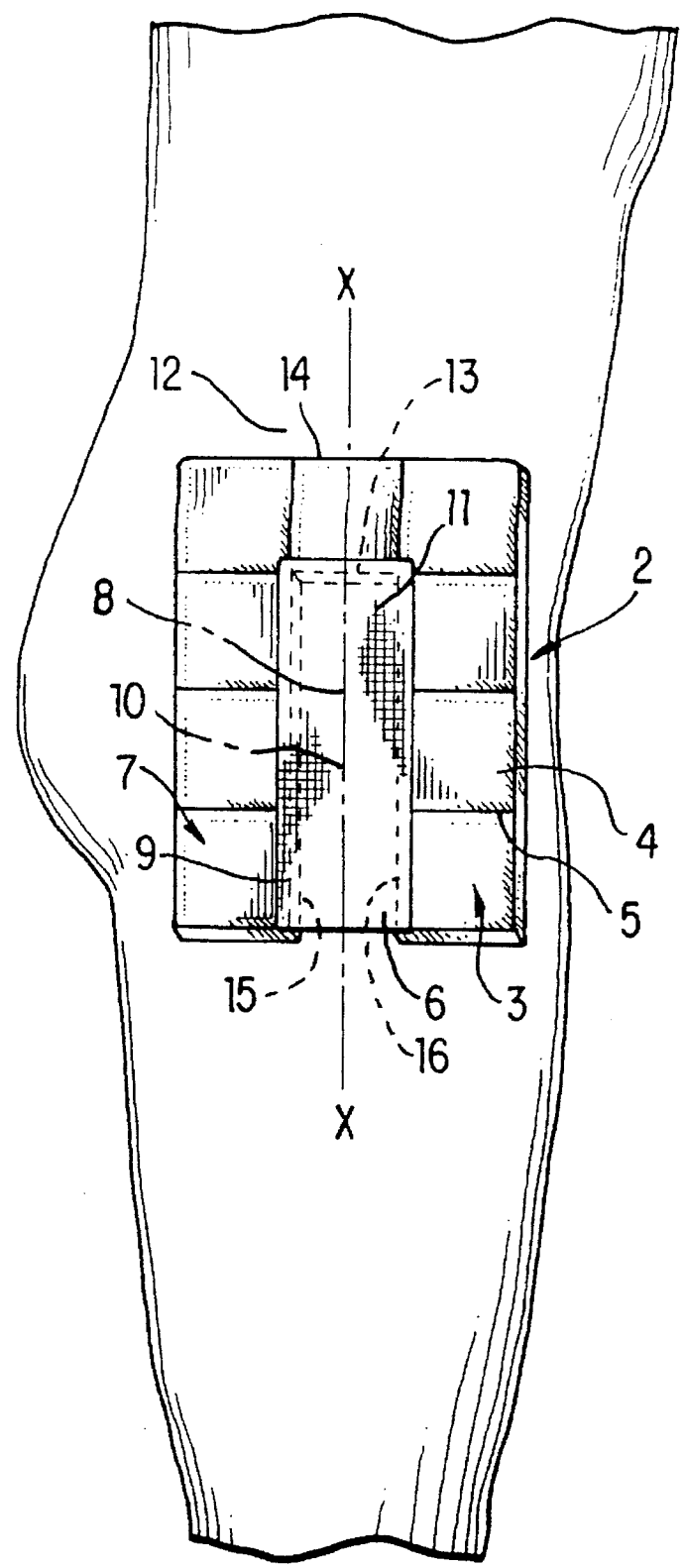
FIG. 2 is a perspective view of an alternate protective garment in accordance with the present invention as worn on the hip of a human subject.

Alternative embodiments of the device may exist where the external border of the device 14 extends a farther or lesser amount than that shown in FIG. 1. For example, FIG. 2 shows an alternative embodiment of a device in accordance with the present invention. In this embodiment, the dimensions and location of the internal open portion of the horseshoe are similar to that described for FIG. 1. However, the number of envelopes containing the shear-thickening material 4 has been reduced to nine, each roughly forming the shape of a square with surface area of approximately 4 cm$^2$. The surface area of the device may also extend well beyond that shown and described for FIG. 1, being limited inferiorly only by the knee, posteriorly by the anal fold or crease between the buttocks, anteriorly by the midpoint of the anterior aspect of the thigh, and superiorly by a point about 10 mm below the superior iliac spine.

In the embodiment of the device shown in FIG. 1 and FIG. 2, the thickness of protective device 2 is constant at approximately 30 mm. However, alternative embodiments of protective device 2 may involve a constant thickness throughout the device between 10–50 mm, or variation in thickness throughout the device between 10–50 mm.

Figure 3:
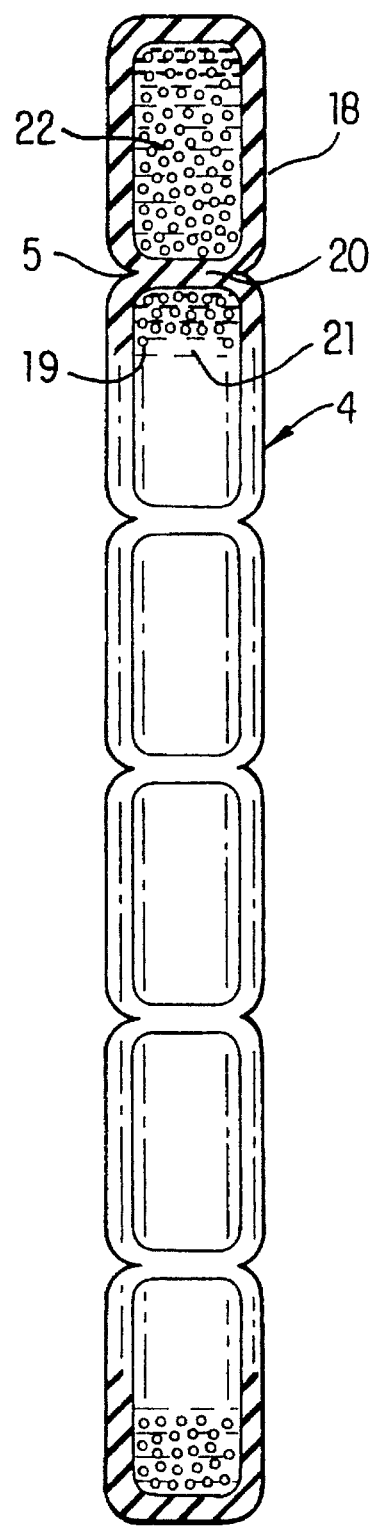
FIG. 3 is a sectional view of a preferred embodiment of the present invention in which the flexible membrane of the garment is subdivided into several envelopes, each containing a shear-thickening material.

FIG. 3 is a sectional view of one preferred embodiment of the present invention in which a flexible and compliant membrane enclosure 18 is subdivided into several and distinct envelopes 4, each containing a shear thickening or dilatant material 22. In this embodiment, membrane 18 is made of an elastomeric polymer such as polyurethane, PVC, latex rubber, or pure gum rubber, having a constant thickness between 0.1–1 mm. A bond 5 exists between contacting surfaces of envelopes 4 adjacent to one another. This bond 5 may be created through various means, including application of an adhesive or a process whereby a chemical reaction or the application of heat or electrical current results in bonding of the membrane material. Each membrane 4 is filled with shear-thickening material 22 at a pressure which causes a small degree of stretch within the membrane material.

Still referring to FIG. 3, shear-thickening material 22 includes a suspension of relatively uniform-sized solid particles 19 (size greatly exaggerated in FIG. 3) in a viscous fluid 21. The properties of solid particles 19 and viscous fluid 21 may vary considerably between different embodiments of the invention. For example, the diameter of particles 19 may vary between 0.1–100 micrometers. The viscosity of the fluid 21 may vary between 1–1,000,000 cP. The ratio of the volume of solid particles 19 to total volume of the material 22 ranges between 20–70 percent.

In one embodiment of the invention, fluid 21 is water and particles 19 are untreated or modified starch granules, where the starch may be corn starch, potato starch, or any plant starch. In another embodiment, particles 19 are plant starch granules, and fluid 21 is a fluid other than pure water. In yet another embodiment, particles 19 are spheres made of a polymer such as polyurethane, polystyrene, or polyvinylchloride and of size 0.1–500 micrometers, and the fluid 21 is water. In yet another embodiment, particles 19 are spheres made of a polymer such as polyurethane, 4 polystyrene, or polyvinylchloride and of size 0.1–500 micrometers, and the fluid 21 is an oil such as silicon or mineral oil having a viscosity between 10 and 1000000 cP.

In still another embodiment, particles 19 are spheres made of a polymer such as polyvinylchloride and of size 0.1–500 micrometers, and the fluid 21 is a plasticizer such as an alkyl phthalate plasticizer.

Figure 7:
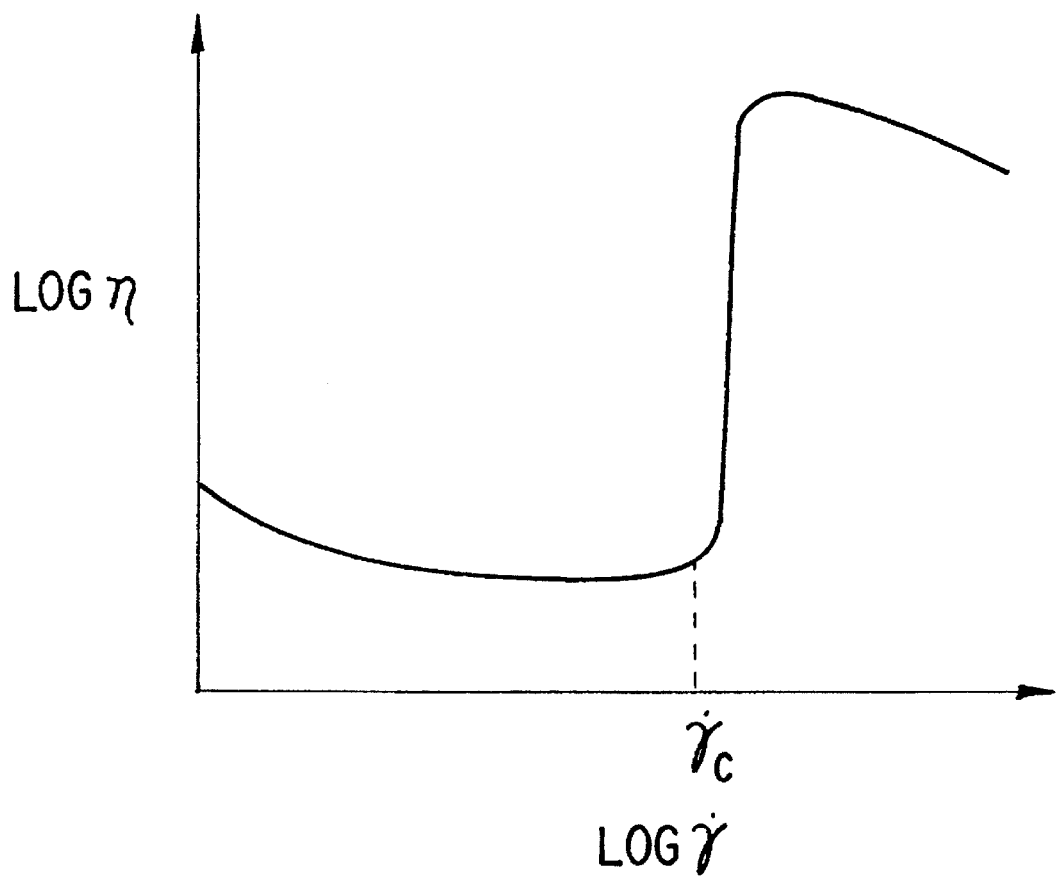
FIG. 7 is a graph showing how the viscosity of the shear-thickening material contained within the present invention changes as a function of shear rate.

It is therefore apparent that shear-thickening material 22 may be formed from a wide variety of particles and fluids. However, its essential feature is an increase in viscosity as a function of shear rate. In particular, the viscosity of material 22 increases dramatically at a relatively well-defined value known as the critical shear rate. This behavior is shown schematically in FIG. 7, where the logarithm of the shear rate $\gamma$ is shown on the horizontal axis and the logarithm of viscosity $\eta$ is shown on the vertical axis. The sudden increase in viscosity at the critical shear rate causes a corresponding increase in the shear stress produced in the material (shear stress is equal to the shear rate multiplied by the viscosity), a measure of its resistance to deformation. In a preferred embodiment of the present invention, the critical shear rate of shear-thickening material 22 is set between 1–100 s$^{-1}$, and typically between 5–30 s$^{-1}$.

In an alternative embodiment of the present invention, the protective device 2 of FIGS. 1 and 2 may be formed into the shape of a horseshoe, and instead of incorporating shear-thickening material, the device is made of a single continuous or several and distinct adjacent members of a elastic or viscoelastic material, such as that sold under the tradename Ensolite.

In yet another alternative embodiment, one or more thin rigid members, possibly formed of a polymeric material such as polyurethane, are affixed to the external surface of protective pad 2, and form a shell which aids in transmitting loads throughout the device.

Figure 4:
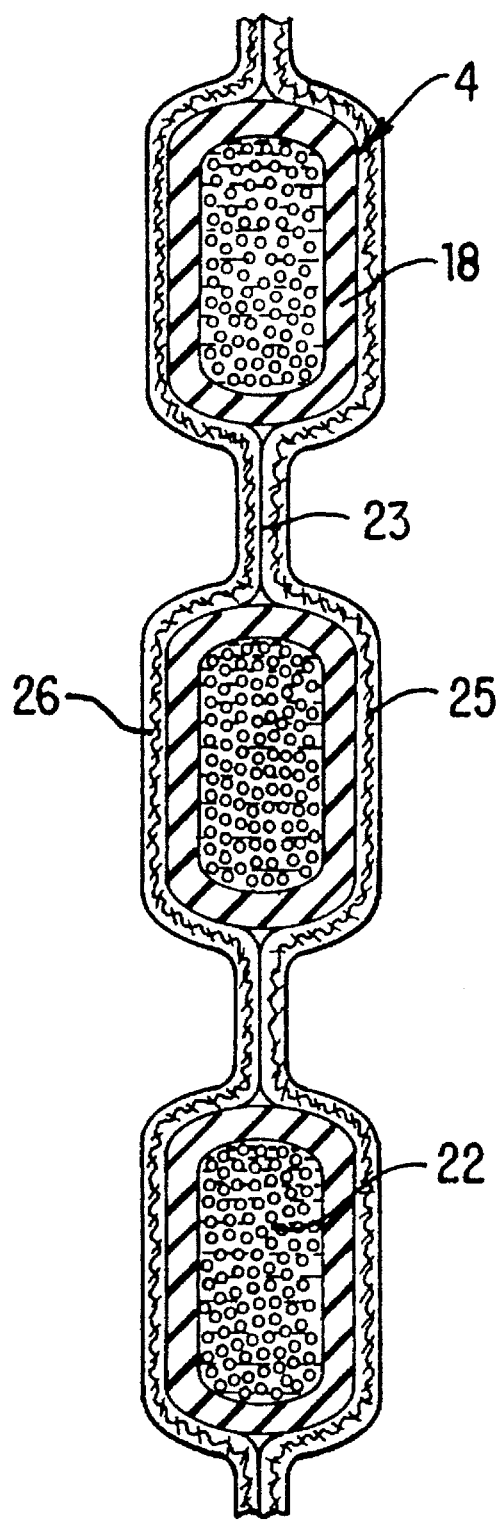
FIG. 4 is a sectional view of an alternate preferred embodiment of the present invention in which a compliant and flexible sleeve surrounds the individual envelopes containing a shear-thickening material.

FIG. 4 is a sectional view of an alternate preferred embodiment of the present invention in which flexible and compliant membrane enclosure 18 is subdivided into several and distinct envelopes 4, each containing shear thickening or dilatant material 22. In this embodiment, envelopes 4 are not bonded together, but enclosed between a compliant and flexible internal sleeve 25 and a compliant and flexible external sleeve 26. In a preferred embodiment, internal sleeve 25 and external sleeve 26 are both constructed of an elastomeric material friendly to the skin such as sold under the SPANDEX trademark. This material preferably should not limit flexibility of the entire pad; accordingly it is sometimes desirable that the product of thickness and elastic modulus for this material be equal to or less than that described above for membrane enclosure 18. In the gap between adjacent envelopes 4, a bond 23 exists between internal sleeve 25 and external sleeve 26, where bond 23 is formed by an adhesive, stitching, or chemical reaction, or the application of heat or electrical current.

Figure 5A:
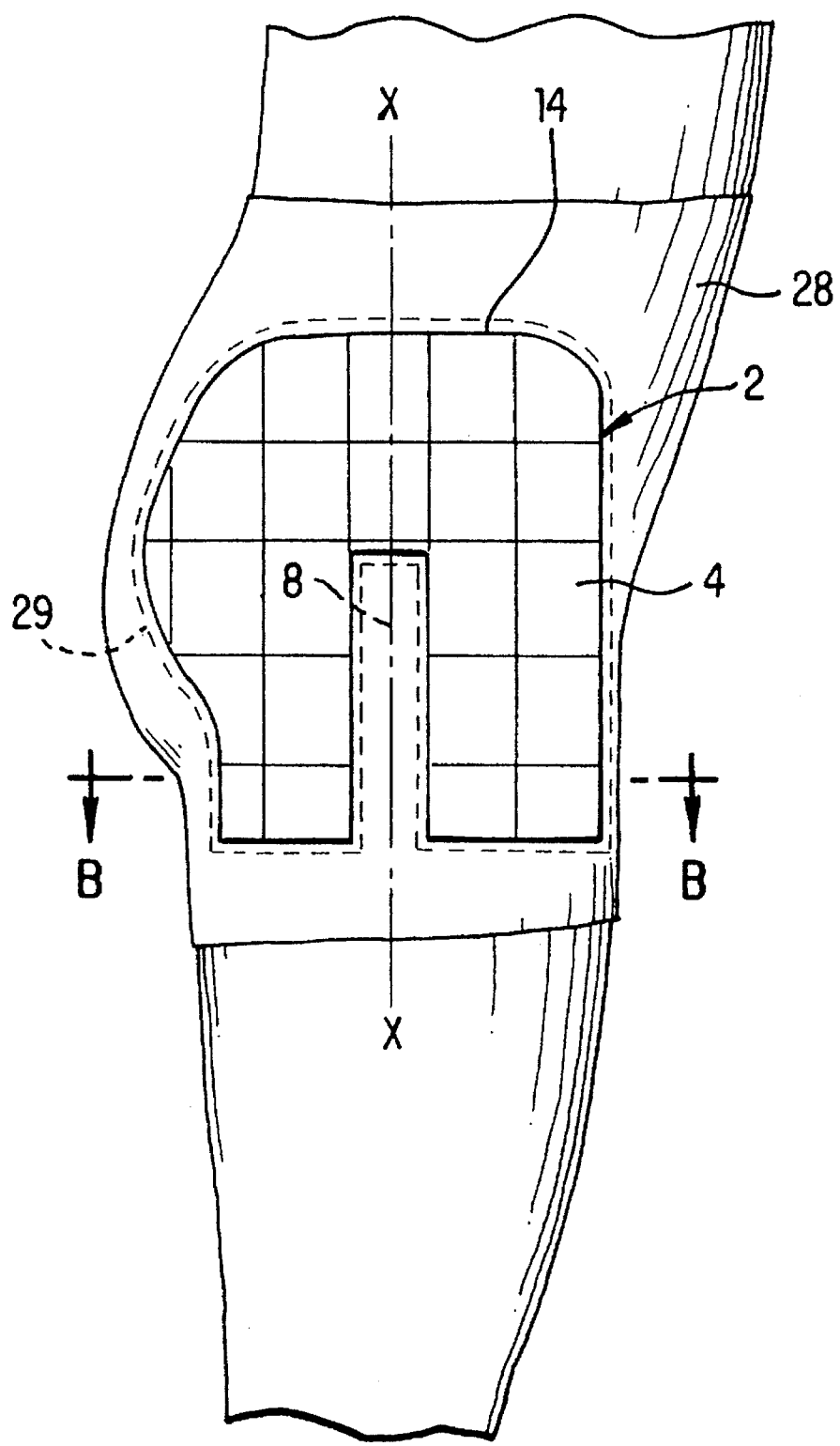
FIG. 5 is a perspective view of a protective garment in accordance with the present invention in the form of shorts for women's or men's wear.
Figure 5B:
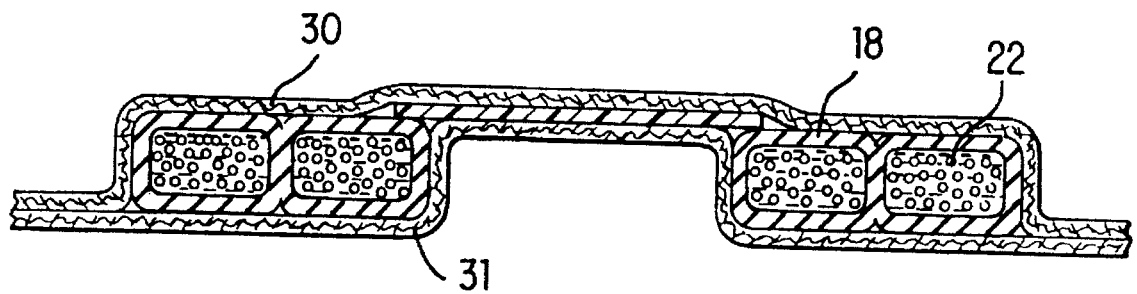

Various methods exist for affixing the hip protective device to the wearer. In one preferred embodiment shown in FIG. 5A, the pad 2 is integrated into a pair of shorts 28 for women's or men's wear. FIG. 5B, shows a cross section of the embodiment of FIG. 5A taken through the plane B—B in FIG. 5A. Shorts 28 are formed of an inner compliant and flexible material 31 and a similar outer compliant and flexible material 30. This material may be SPANDEX or a similar material. The shorts are sized to fit snugly around the wearer, with both inner material 31 and outer material 30 in a state of stretch during normal wear. Hip protective device 2 is secured into shorts 28 by a bond 29 around the perimeter of the pad 2. As in other embodiments, the pad has envelopes 4 containing within membrane 18 shear-thickening material 22.

Several different embodiments exist with respect to the arrangement of short pants 28 and the integration of protective device 2 within the pants. In one potential embodiment, bond 29 is permanent and formed of stitching or an adhesive material, while in another embodiment all or a portion of bond 29 is easily broken and reformed, as would be provided if the bond was formed of a hook-and-pile material such as that sold under the name VELCRO. This latter embodiment allows easy insertion and removal of protective device 2 into short pants 28 to facilitate easy cleaning of short pants 28 or replacement of protective device 28, if required.

Furthermore, in one embodiment short pants 28 are continuous, while in another embodiment short pants 28 are crotchless, thus facilitating use by individuals suffering from incontinence.

Figure 6:
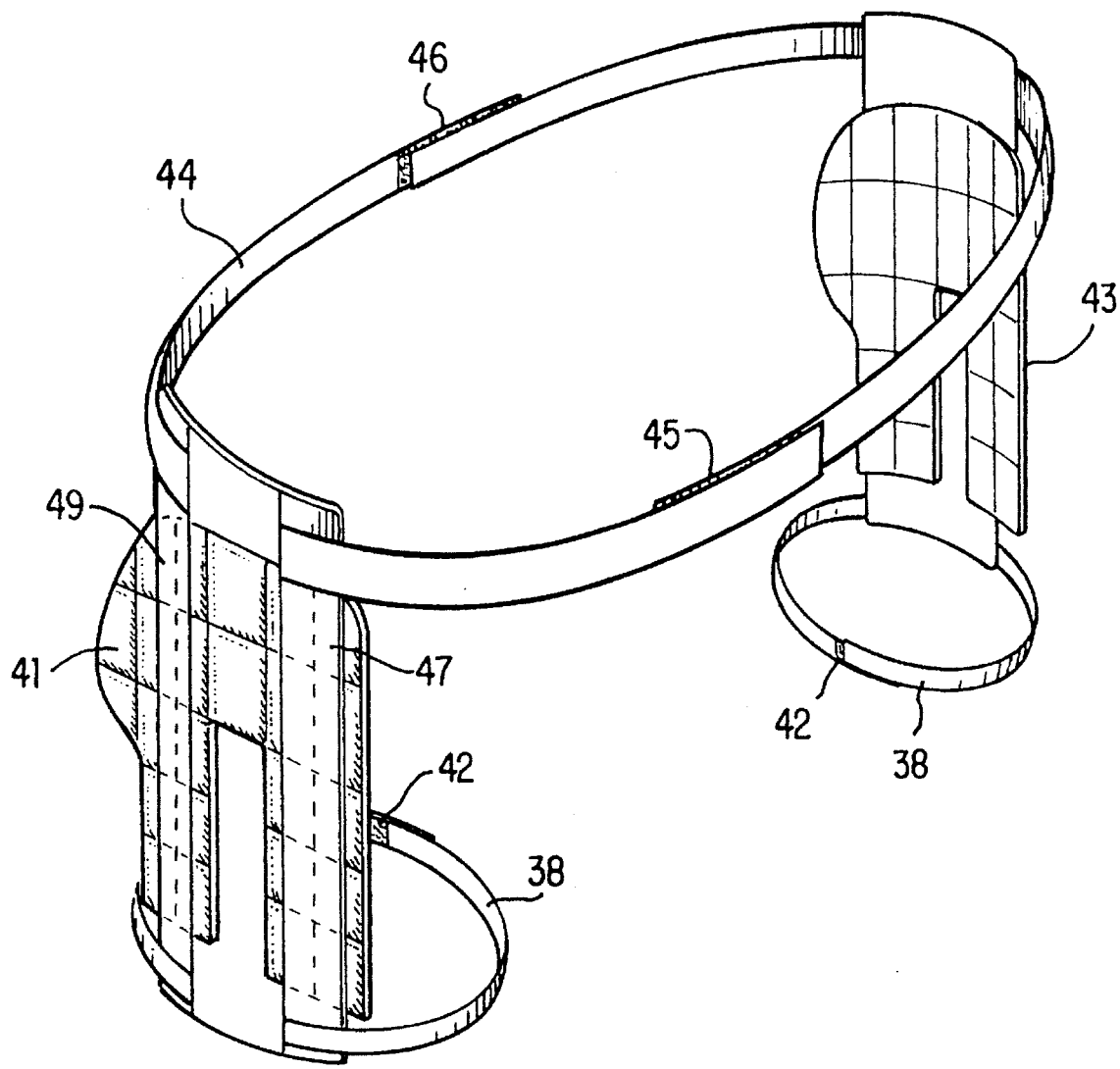
FIG. 6 is a perspective view of a protective garment in accordance with the present invention which utilizes waist and thigh belts for affixing the device over the hip regions.

FIG. 6 is a perspective view of an alternate method of affixing over the hip region a protective garment in accordance with the present invention. In this arrangement, a confirmed waist belt 44 having right and left portions, mounts a pair of protective pads 41 and 43 on the right and left hips respectively. The right and left portions of the belt are joined by anteriorly located, mating hook-and-pile strips 45 and posteriorly located, mating hook-and-pile strips 46. Similarly, conformed thigh belts 38 are used to affix the bottom portions of the protectors 41 and 43, and are adjusted by means of mating hook-and-pile strips 42. Similar hook-and-pile mating strips may be used to attach the ends of the waist and thigh belts to the external surface of the protective pads 41 and 43. In this connection, vertical strips 47 and 49 of pile are provided on the protective pads 41 and 43 and corresponding strips of hooks are provided on the belts to properly and securely locate protective pads 41 and 43 over the hip region.

Another method for affixing the device to the hip involves securing an adhesive layer over the internal surface of the pad which opposes the skin. This adhesive layer bonds to both the pad and the skin, and allows precise placement of the protective device over the hip. This method for affixing the device may be particularly suited to those persons at greatest risk for suffering falls and thus in need of constant protection. Depending on the properties of the adhesive, the device may be mounted for a number of days or weeks, while being removed periodically to allow washing of the underlying skin.

The present invention can also be applied towards prevention of fractures of bones other than the femur, such as the radius, ulna, and tibia. For example, FIG. 8 displays a protective device 58 embodied in accordance with the present invention and designed to protect against fracture or injury of the ulna in sporting activities such as football, where protective devices of this type are currently worn, or during any other activities where such protection is desired. Typically the device may be positioned between the ulna's head 62 and the tip 60 of the ulna's olecranon process. The device includes a laterally and medially located strips 64 and 66 respectively of flexible envelopes containing shear-thickening material. A rigid shell 68 formed of a polymeric material is adhered by an adhesive so as overlie the external surface of strips 64 and 66 so that a gap is formed between shell 68 and the skin overlying the ulna. As a result of this construction, upon impact to the shell 68, the energy of impact is spread away from the ulna and into the soft tissues underlying strips 64 and 66, thus protecting the ulna from injury. A sleeve 70 formed of a flexible, elastic material is adhered to shell 68 by means of a glue or adhesive, and aids in maintaining proper positioning of protective device 58 over the ulna.

Figure 8:
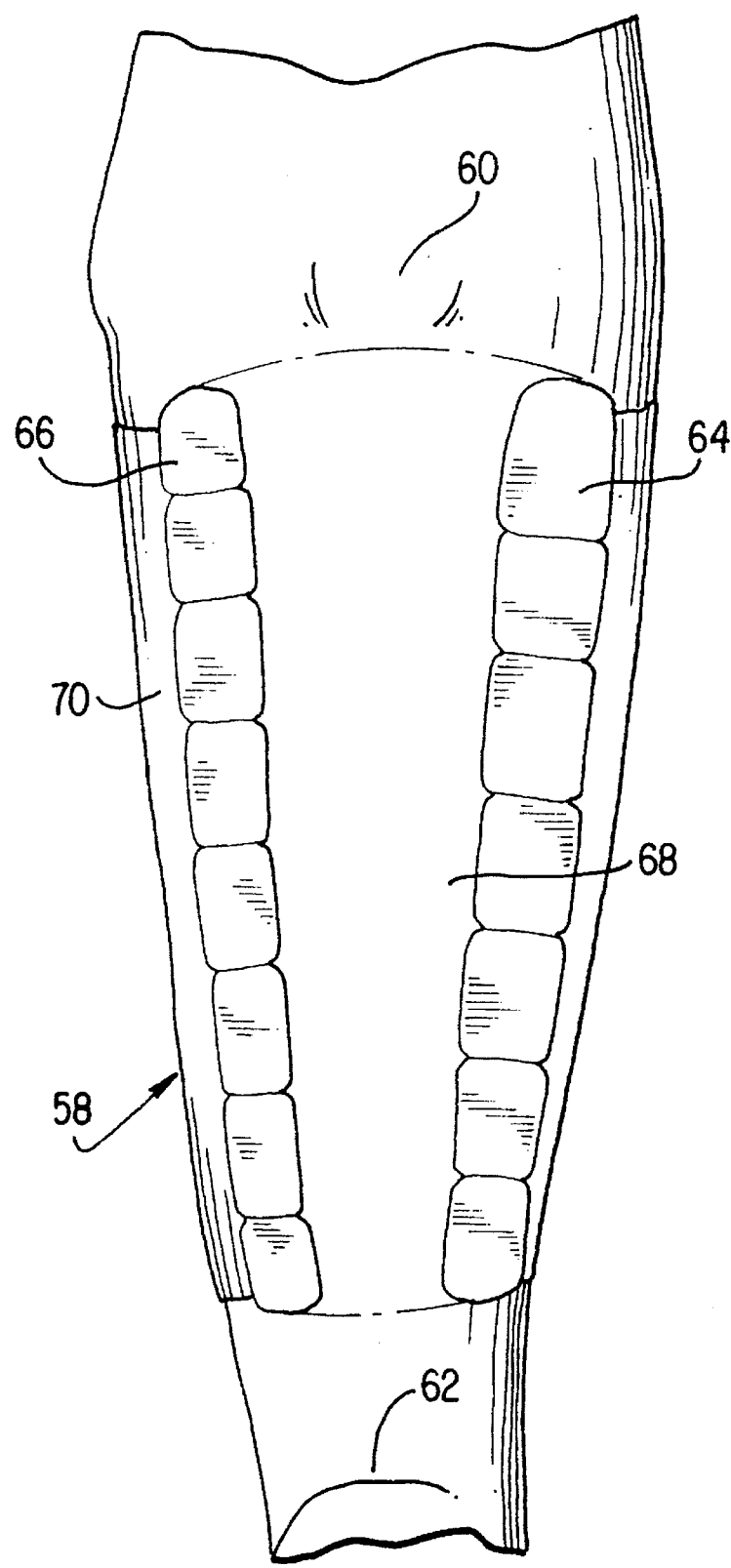
FIG. 8 is a top view of a protective garment in accordance with the present invention for preventing injury to the ulna bone.

In another embodiment of the present invention, designed to serve as shin guards for sports such as soccer, an arrangement similar to that shown in FIG. 8 for protecting the ulna, here provided for the tibia, and is thus worn over the anterior shin. In this arrangement, two strips of envelopes containing shear-thickening material are placed in parallel with the tibia on both medial and lateral sides. As in the case for the ulna, a rigid shell is adhered over these strips so that a gap exists between the shell and the underlying tibia.

Figure 9:
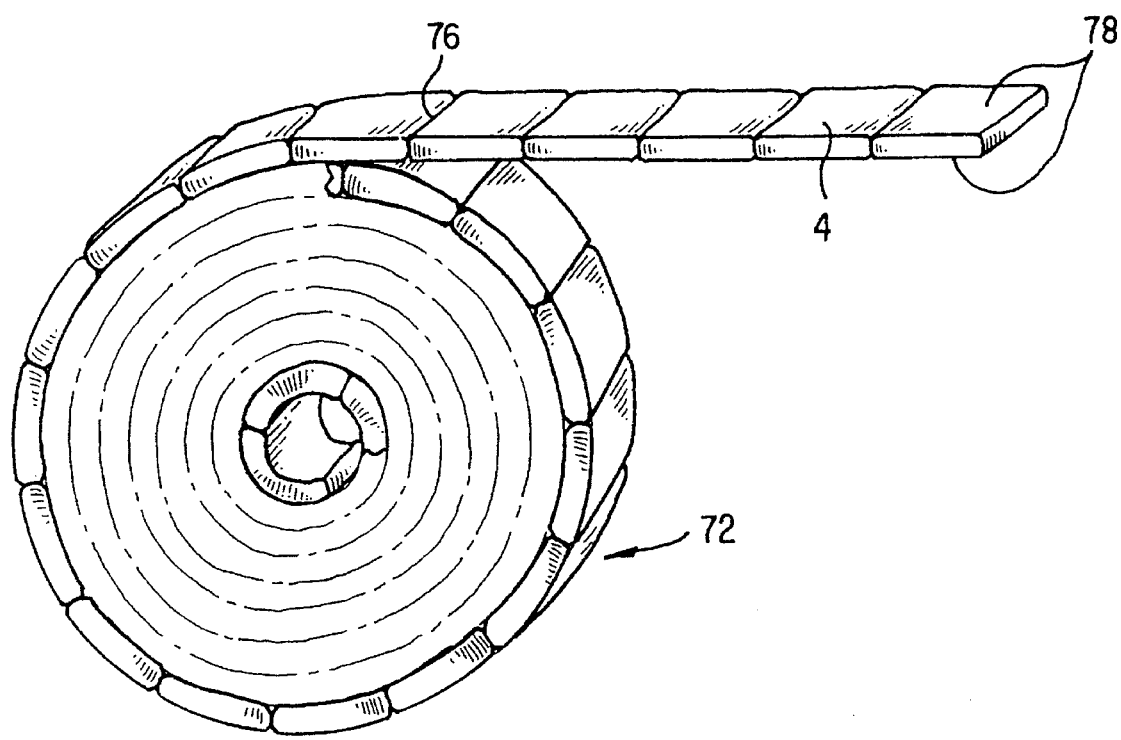
FIG. 9 is a perspective view of a roll of envelopes containing shear-thickening material in accordance with an embodiment of the present invention for use in the customized design of protective garments.
Figure 10:
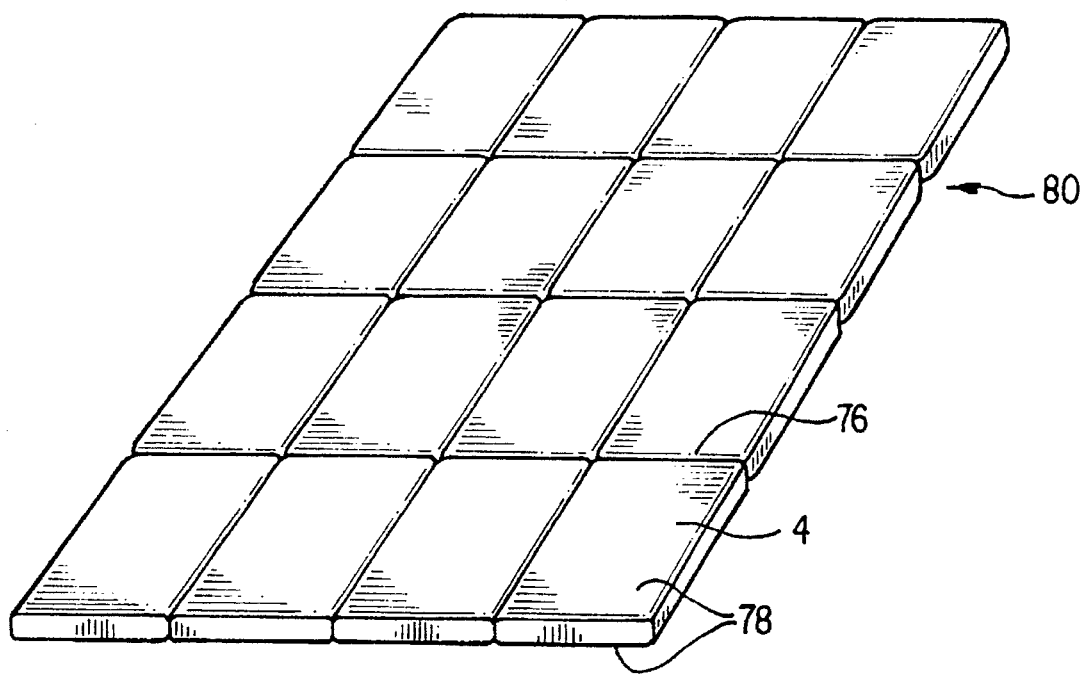
FIG. 10 is a perspective view of an alternate embodiment in accordance with the present invention in which is provided a flat array of envelopes containing shear-thickening material for use in the customized design of protective garments.

In a further embodiment of the present invention, envelopes 4 containing shear-thickening material 22 are made available for the customized design of protective devices, either for the general prevention of injuries during sporting or other activities or for preventing further injury or pain from impact to a previously injured and therefore sensitive location. FIGS. 9 and 10 show two possible arrangements in which this product might be supplied. FIG. 9 shows a roll 72 of envelopes 4, each containing shear thickening material. Dual-sided adhesive tape 78 is adhered to both the front and back sides of the envelopes. A layer of waxpaper or similar matter is used to cover at least the outword facing side of adhesive tape 78. Scissors can be used to cut along a junction 76 between adjacent envelopes, and thus produce a strip of envelopes 4 of desired length. After then removing the waxpaper layers covering the adhesive tape 78, envelopes 4 can be mounted directly to the skin and a rigid shell can be mounted over envelopes 4. If required, further adhesive tape, elastic straps, or some other means may be utilized to supplement adhesive tape 78 in securing envelopes 4 to the desired location on the body.

FIG. 10 displays an alternative method by which envelopes 4 may be supplied, including a flat sheet 80 of envelopes 4 arranged in close proximity to one another. Again, scissors may be used to cut along junctions 76 to produce a protective device of the desired shape.

Figure 11:
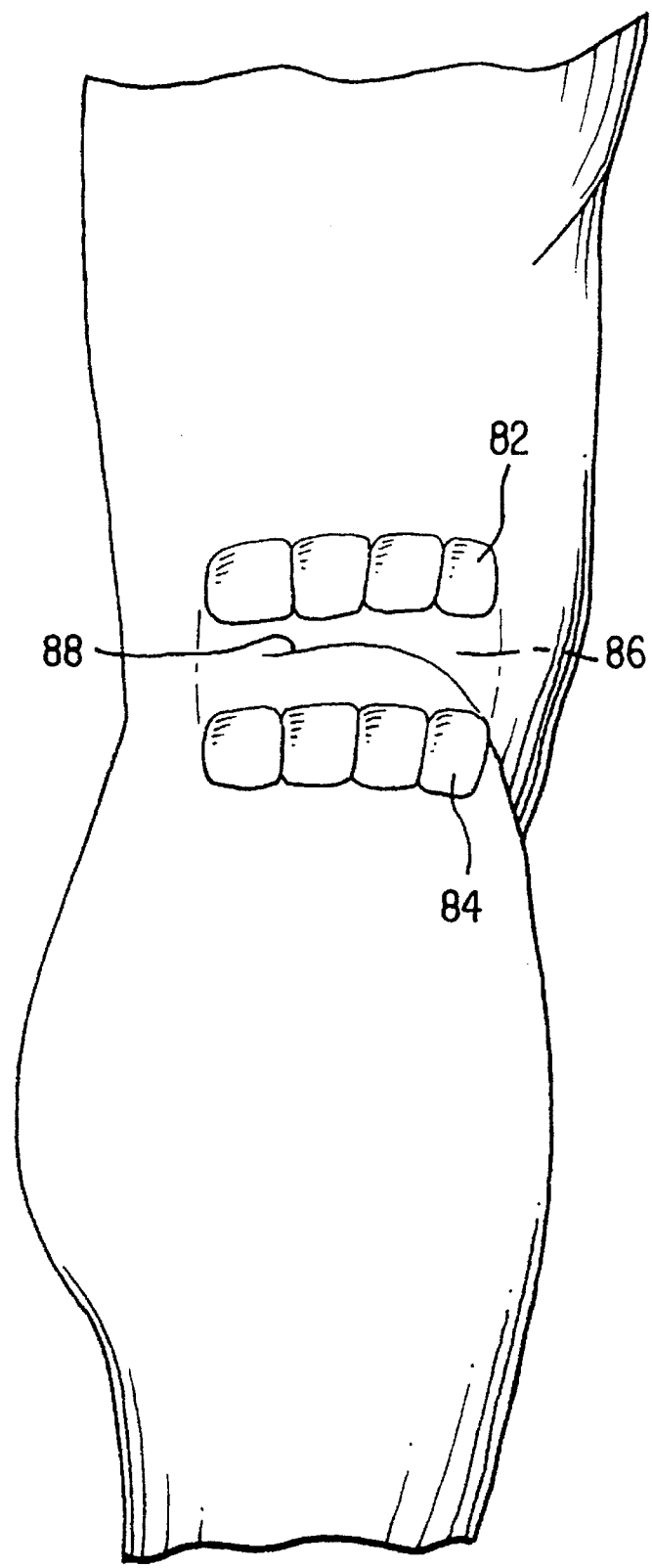
FIG. 11 is a perspective view of a protective garment that has been customized in accordance with an embodiment of the present invention for use in preventing injury to the iliac spine.

FIG. 11 shows one of the several possible customized protective devices capable of being formed from the embodiments of FIGS. 9 and 10. In this case, a device has been constructed to protect against further injury or pain from impact to the iliac crest 88, which is often injured in sporting activities such as football, basketball, or hockey (the injury is often referred to as a "hip pointer"). The device here includes a superior strip 82 of envelopes containing shear-thickening material, and an inferior strip 84 of envelopes containing shear-thickening material. A rigid shell 86 is adhered over the external surface of strips 82 and 84, and overlies iliac crest 88. Since shear-thickening material is fluid under low rates of loading, a continuous contact area is formed between the underlying skin and strips 82 and 84. Upon impact to the rigid shell, shear-thickening material stiffens, and shunts the impact energy into the soft tissues underlying strips 82 and 84, thereby protecting the vulnerable iliac crest region 88.

The effectiveness of a hip fracture prevention garment depends on the ability of the garment to lower the peak force applied to the femur in a fall to a value significantly below the mean force required to fracture the elderly femur (2040N). In order to realistically assess the attenuation in femoral impact force provided by the device, it must be tested under conditions which simulate the interaction between the device and the underlying skeletal and soft tissues. A common fault in estimating the force attenuation provided by hip protective devices is to disregard the role of the soft tissues between the femur and the protective device. For example, Ferber, in U.S. Pat. No. 4,807,301, describes testing the force attenuating capacity of the energy-absorbing material to be placed over the greater trochanter in his preferred embodiment by dropping a steel weight onto the material from a 24-inch height. He then appears to assume the same degree of force attenuation is provided when the pad is worn over the hip in a fall. However, this will result in overestimation of the actual force attenuation provided by the protective device during a fall on the hip, since a steel weight is many times more rigid than the human hip. To obtain a reasonable estimate of this attenuation, one requires knowledge and incorporation of the compliance of the unpadded hip. Wortberg, in his U.S. Pat. No. 4,573,216, appears to account for the compliance of the femur, cartilage of the hip joint, and the overlying skin in estimating the force attenuation provided by the protective device. However, he does not account for the compliances of the fat and muscle overlying the trochanteric region, or the compliance of the pelvis.

To evaluate and compare the protective ability of the present invention with that provided by prior art protective devices, we have measured the impact force attenuation provided by several different hip protective devices. These included the following prior art hip protective devices: (1) a commercially available device formed of an energy-absorbent foam and rigid external shell, designed to cover the greater trochanter and surrounding area, and having a maximum thickness of approximately 32 mm ("Impant" pad, Dr. L. Proshek, Edina, Minn.); (2) a protective appliance constructed by Strock in accordance with his U.S. Pat. No. 4,926,883 and of maximum thickness 35 mm; (3) a protective appliance constructed by Ferber in accordance with his U.S. Pat. No. 4,926,883 and of maximum thickness 11 mm; (4) a protective appliance constructed by Wortberg in accordance with his U.S. Pat. No. 4,926,883 and of maximum thickness 38 mm. In addition, the following embodiments of the present invention were tested: (1) a horseshoe-shaped device constructed of a viscoelastic foam sold under the trademark Ensolite, and having a maximum thickness of 25 mm; (2) a horseshoe-shaped device constructed of a shear-thickening corn starch-water mixture, and having a maximum thickness of 35 mm; and (3) a horseshoe-shaped device constructed of a shear-thickening corn starch-water mixture, and having a maximum thickness of 49 mm. These tests have provided data regarding the ability of these pads to attenuate femoral impact force, and thus reduce the probability of hip fracture occurrence during a fall on the hip. The results of these tests indicate that, while each strategy accomplishes attenuation of femoral impact force, only a device in accordance with the present invention reduces this force to a value below that required to fracture the elderly femur.

Figure 12:
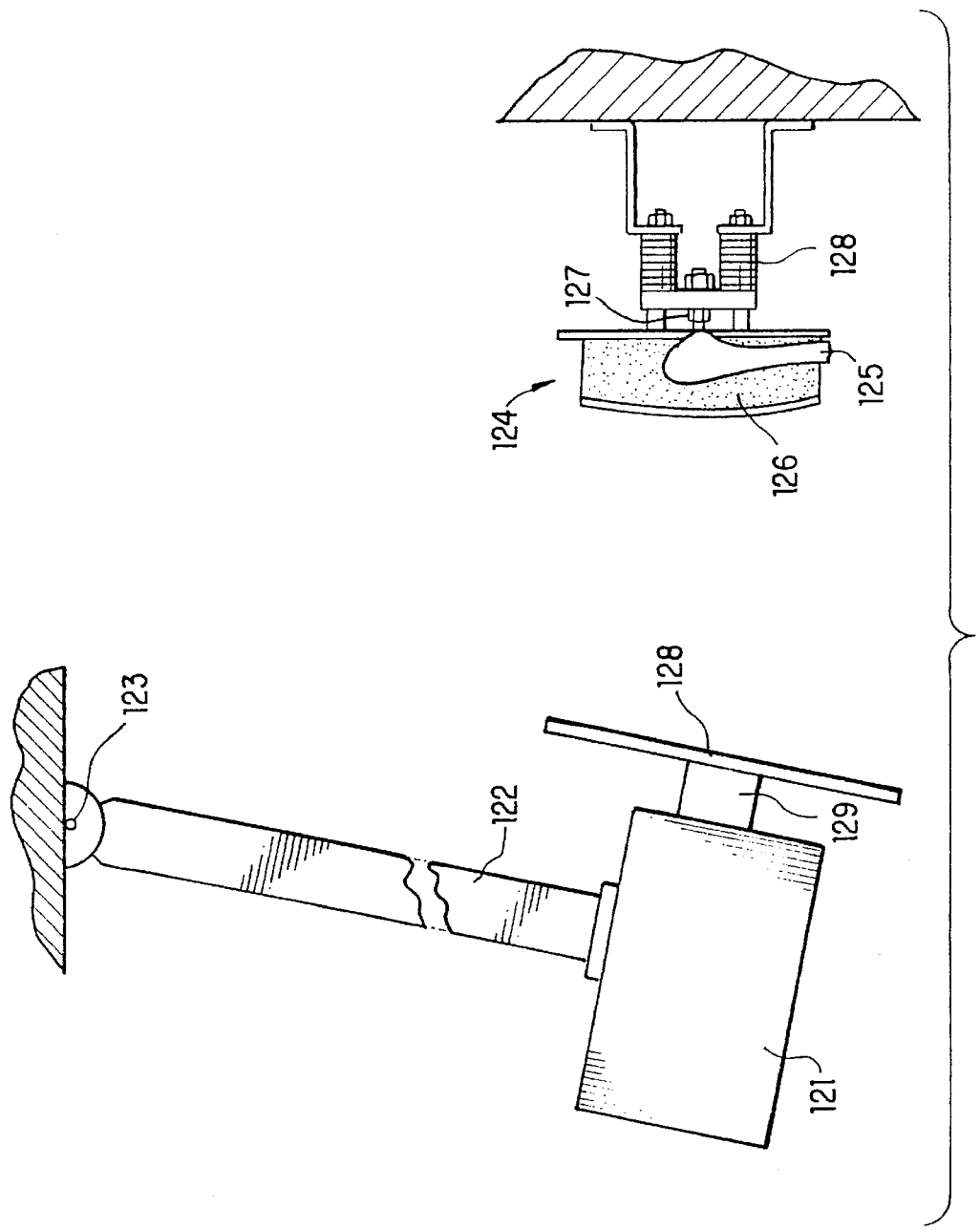
FIG. 12 is a side view of the impact pendulum and surrogate human pelvis used in testing the force attenuating capabilities of both the present invention and prior art hip protective devices.

The testing system is shown in FIG. 12, and includes an impact pendulum (including a mass 121, arm 122, pivot 123, and head 128) and surrogate pelvis 124 designed to match the typical female pelvis in surface anatomy, local soft tissue stiffness, and pelvic compliance. The surrogate pelvis 124 includes a surrogate femur 125 surrounded by foam 126 to simulate behavior of soft tissue. A load cell 127 producing a signal to measure force on the femur 125, and a pelvic spring 128 simulates the effect of pelvic compliance. The surrogate pelvis allowed us to evaluate pad performance based on the combined response of the hip pad and the underlying skeletal and soft tissue structures. The polyurethane foams forming the soft tissues of the surrogate were selected to match the regional variation in soft tissue stiffness exhibited by females during indentation tests over the trochanteric, gluteus, and anterior thigh regions. Mean values of stiffness at 60N (which ranged from 35±13.9 kN/m over the greater trochanter to 8.5±2.9 kN/m over the posterolateral buttock) were matched on average to within 35% during tests at corresponding locations on the surrogate. Pelvic compliance was simulated by neoprene springs 128, providing the entire unit with an effective stiffness of 83 kN/m, within 18% of that measured in females undergoing simulated falls on the hip (Robinovitch, S. N., Hayes, W. C., McMahon, T. A., J Biomech Eng, 113: 366–374, 1991). In all experiments, the pendulum head was directed to impact the lateral aspect of the greater trochanter. Total externally applied force was measured by a load cell 129 on the pendulum, while the force delivered through the soft tissues to the hip was measured with the load cell 127 mounted on the femur. Pendulum impact velocity was 2.6 m/s, similar to the average hip impact velocity measured in human volunteers falling on their hip. Pendulum mass was 35 kg, matching the average effective mass of the body during impact to the hip [Robinovitch, S. N., Hayes, W. C., McMahon, T. A., J Biomech Eng, 113: 366–374, 1991]. The kinetic energy of the pendulum at the moment of impact was therefore 120 Joules.

Figure 13:
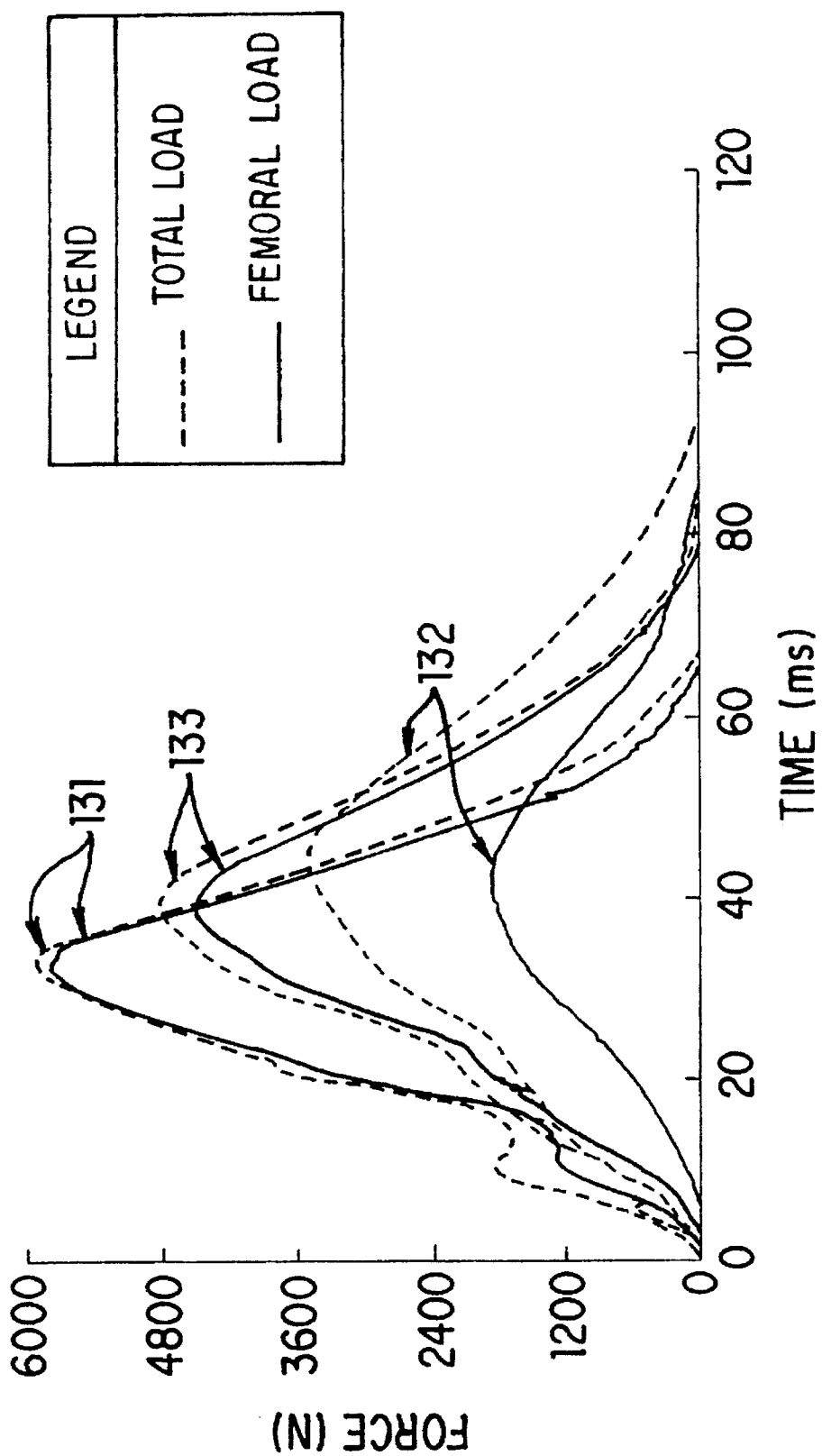
FIG. 13 is a line graph comparing total applied force and femoral force as functions of time when 120 Joules of impact energy is applied to a surrogate pelvis alone, and after affixing to the pelvis a device in accordance with an embodiment of the present invention, and also after employing a device in accordance with U.S. Pat. No. 4,573,216.

FIG. 13 is a line graph of experimental results. Force is plotted on the vertical axis of the graph, and time is plotted on the horizontal axis of the graph. Both total externally applied force and total femoral force are shown, the former in dotted lines and the latter in solid lines. For clarity, the results from only three impact tests are shown. These include: (1) impact to the unpadded surrogate pelvis (shown by curves 131); (2) impact to the surrogate pelvis after affixing to the skin of the pelvis the horseshoe shaped device in accordance with the present invention, incorporating a shear-thickening corn starch-water material, and possessing a maximum thickness of 35 mm (shown by curves 132); and (3) impact to the surrogate pelvis after affixing to the skin of the pelvis the device in accordance with Wortberg's U.S. Pat. No. 4,573,216 and possessing a maximum thickness of 38 mm. Note in the unpadded case, peak total external applied force was 5960N and peak femoral force was 5770N. In each set of curves, the total load is shown by a dashed line, and the femoral load is shown by a solid line.

The Wortberg pad (which provides a degree of force attenuation typical of all prior art pads tested), reduces peak externally applied force by 20% to 4770N and peak femoral force by 22% to 4500N. In comparison, the horseshoe pad of 35 mm maximum thickness reduces peak externally applied force by 39% to 3590N, while reducing peak femoral force by 68% to 1840N. Not shown are the results for impacts to the horseshoe pad of 49 mm maximum thickness, which reduces peak externally applied force by 36% to 3800N, and peak femoral force by 88% to 700N.

Figure 14:
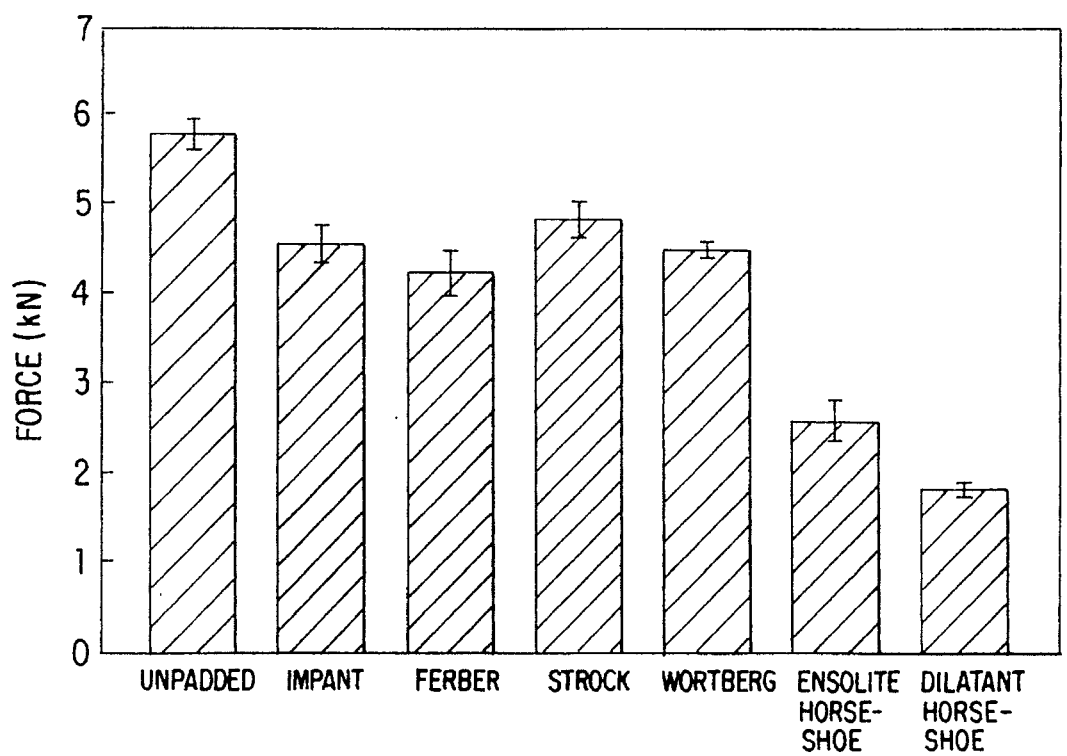
FIG. 14 is a bar graph comparing peak total applied force and peak femoral force when 120 J of impact energy is applied to the surrogate pelvis alone, and after affixing to the surrogate pelvis a commercially available protective hip garment (Impant pad, developed by Dr. L. Proshek, Edina, Minn.), three different, previously patented hip protective devices (U.S. Pat. Nos. 4,926,883, 4,573,216, and 4,807, 301), and two devices in accordance with embodiments of the present invention.

FIG. 14 is a bar graph which displays the peak force applied to the femur during impact to each of the systems tested. Note the horseshoe shaped device constructed of Ensolite foam and possessing a maximum thickness of 25 mm lowered peak externally applied force by 33% and peak femoral force by 55%. In comparison, the Impant device reduced peak externally applied force by 18% and peak femoral force by 21, a device in accordance with U.S. Pat. No. 4,926,883 reduced peak externally applied force by 14% and peak femoral force by 16% and a device in accordance U.S. Pat. No. 4,807,301 reduced peak externally applied force by 17% and peak femoral force by 27%. The results of these tests show that, when compared to the next most effective prior art hip protective device, the device in accordance with the present invention provides nearly a twofold greater reduction in peak externally applied force, and a threefold greater attenuation in peak femoral impact force. The results also suggest that when worn during a typical fall on the hip, the horseshoe device in accordance with the present invention has the ability to lower femoral impact force to a value below the mean force required to fracture the elderly femur (2040N). Conversely, with all prior art devices tested, peak femoral force remained above twice the mean force required to fracture the elderly femur. It therefore appears that the present invention lowers the probability of suffering a hip fracture during a fall on the hip to a much greater extent than all tested prior art pads.

What is claimed is:

1. A garment, for reducing the risk of bone fracture of a human or animal subject due to impact forces on a vulnerable region having a bone part near the skin surface, there being a soft tissue region proximate to the vulnerable region and lacking a bone part near the skin surface, the garment comprising:

shear thickening material disposed in at least one compliant enclosure shaped, in accordance with anatomical features of the vulnerable region and the soft tissue region, so as to shunt a substantial portion of the impact energy from the vulnerable region to the soft tissue region, where such energy may be safely dissipated; and mounting means for removably mounting the at least one compliant enclosure on the subject in a manner permitting the shunting of impact energy from the vulnerable region to the soft tissue region.

2. A garment according to claim 1, wherein:

the at least one compliant enclosure is arranged to overlie the soft tissue region but not the vulnerable region, for receiving the impact energy from the vulnerable portion and retransmitting a substantial portion of the impact energy to the soft tissue region and the mounting means include means for mounting the at least one compliant enclosure so as to overlie the soft tissue region but not the vulnerable region.

3. A garment according to claim 2, wherein the at least one compliant enclosure is arranged in a horseshoe shape including two arms and defining an exposed interior area between the two arms, the interior area coinciding generally with the vulnerable region when the garment is mounted on the subject.

4. A garment according to claim 2, wherein the at least one compliant enclosure has an annular shape, with the interior area coinciding generally with the vulnerable region when the garment is mounted on the subject.

5. A garment according to claim 1, wherein the shear-thickening material is relatively stiff during the time of impact but relatively fluid at other times.

6. A garment according to claim 1, wherein the shear-thickening material has a critical shear rate between 5 and 30 $s^{-1}$.

7. A garment according to claim 1 wherein the at least one compliant enclosure comprises at least one envelope of an elastomeric material.

8. A garment according to claim 1 wherein the at least one compliant enclosure comprises a plurality of adjacent sub-envelopes, each sub-envelope containing a portion of the shear-thickening material.

9. A garment according to claim 1, wherein the shear-thickening material comprises an aqueous suspension of plant starch.

10. A garment according to claim 9, wherein the aqueous suspension has a solid volume fraction between 20 and 70 percent.

11. A garment according to claim 1, wherein the shear-thickening material comprises a suspension of spheres in water.

12. A garment according to claim 11, wherein the spheres are made of a plastic selected from the group consisting of polyurethane, polystyrene, and polyvinylchloride.

13. A garment according to claim 11, wherein the spheres have a size lying between 0.1 and 500 micrometers in diameter.

14. A garment according to claim 1, wherein the shear-thickening material is a suspension of spheres that includes a composition selected from the group consisting of polyurethane, polystyrene, and polyvinylchloride, in a plasticizer.

15. A garment according to claim 14, wherein the plasticizer is an alkyl phthalate.

16. A garment according to claim 1, wherein the mounting means includes a pair of short pants in which is disposed the at least one compliant enclosure.

17. A garment according to claim 1, wherein the mounting means includes a plurality of belts coupled to the at least one compliant enclosure.

18. A garment according to claim 1, wherein the mounting means includes adhesive means for adhering the at least one compliant enclosure to the body of the subject.

19. A kit for fabrication of an energy shunting device, the kit comprising:

a plurality of envelopes, each envelope containing shear-thickening material and having a face with adhesive disposed thereon, the envelopes disposed contiguously with respect to one another in a linear array permitting the envelopes to be stored in a roll and formed from a common set of components.

20. A garment, for reducing the risk of bone fracture of a human or animal subject due to impact forces on a greater trochanter disposed in a hip of the human or animal subject, said greater trochanter being at the end of a femur and wherein the hip has a soft tissue region proximate to the greater trochanter and the femur and lacking a bone part near the skin surface, the garment comprising:

an energy shunting pad in the shape of a horseshoe including two arms and defining an exposed interior area between the two arms, the interior area coinciding generally with the greater trochanter and the femur when the garment is mounted on the subject; and mounting means for removably mounting the energy shunting pad on the subject with the two arms proximate to opposing sides of the femur so that a substantial portion of impact energy directed at the hip of the subject is shunted from the greater trochanter to the soft tissue region where such energy may be safely dissipated.

21. A garment according to claim 20 wherein the energy shunting pad comprises a shear-thickening material.

22. A garment according to claim 21 wherein the shear-thickening material has a critical shear rate between 5 and 30 $s^{-1}$.

23. A garment according to claim 21 further comprising an envelope of an elastomeric material in which is disposed the shear-thickening material.

24. A garment according to claim 21 further comprising a plurality of adjacent sub-envelopes, each sub-envelope containing a portion of the shear-thickening material.

25. A garment according to claim 20 wherein the mounting means includes a pair of short pants in which is disposed the energy shunting pad.

26. A garment according to claim 20 where the mounting means includes a plurality of belts coupled to the energy shunting pad.

27. A protective pad comprising:

shear-thickening material disposed in at least one compliant enclosure configured with two arms, defining an exposed area between the arms at which the distance between the two arms is between 30 mm, and 70 mm., about a vulnerable region to be protected such that the at least one compliant enclosure overlies two opposing regions both adjacent to the vulnerable region but not the vulnerable region itself, said at least one compliant enclosure serving to receive impact energy directed toward the vulnerable region and retransmitting a substantial portion of the impact energy to the adjacent region.

28. The protective pad of claim 27 wherein the at least one compliant enclosure is arranged in a horseshoe shape including the two arms.

29. The protective pad of claim 27 wherein the at least one compliant enclosure has an annular shape, with the interior area coinciding generally with the vulnerable region to be protected by the pad.

30. The protective pad of claim 27 wherein the shear-thickening material has a critical shear rate between 5 and 30 $s^{-1}$.

31. The protective pad of claim 27 further comprising adhesive means for adhering the at least one compliant enclosure to the body of a subject.

32. A garment, for reducing the risk of bone fracture of a human or animal subject due to impact forces on a vulnerable region having a bone part near the skin surface, the vulnerable region being proximate to a soft tissue region lacking a bone part near the skin surface, the garment comprising:

shear thickening material disposed in at least one compliant enclosure for shunting a substantial portion of the impact energy from the vulnerable region to the soft tissue region, where such energy may be safely dissipated; and adhesive means for removably adhering the at least one compliant enclosure to the body of the subject.

33. A garment, for reducing the risk of bone fracture of a human or animal subject due to impact forces on a vulnerable region having a bone part near the skin surface, the vulnerable region being proximate to a soft tissue region lacking a bone part near the skin surface, the garment comprising:

shear thickening material disposed in at least one compliant enclosure for shunting a substantial portion of the impact energy from the vulnerable region to the soft tissue region, where such energy may be safely dissipated, the shear thickening material comprising a suspension of spheres in water; and mounting means for removably mounting the at least one compliant enclosure on the subject.

34. A garment according to claim 33, wherein the spheres are made of a plastic selected from the group consisting of polyurethane, polystyrene, and polyvinylchloride.

35. A garment according to claim 33, wherein the spheres have a size lying between 0.1 and 500 micrometers in diameter.

36. A garment, for reducing the risk of bone fracture of a human or animal subject due to impact forces on a vulnerable region having a bone part near the skin surface, the vulnerable region being proximate to a soft tissue region lacking a bone part near the skin surface, the garment comprising:

shear thickening material disposed in at least one compliant enclosure for shunting a substantial portion of the impact energy from the vulnerable region to the soft tissue region, where such energy may be safely dissipated, the shear-thickening material comprising a suspension of particles that includes a composition selected from the group consisting of polyurethane, polystyrene, and polyvinylchloride, in a plasticizer; and mounting means for removably mounting the at least one compliant enclosure on the subject.

37. A garment according to claim 36, wherein the plasticizer is an alkyl phthalate.

38. A protective pad comprising:

shear-thickening material disposed in at least one compliant enclosure configured in an annular shape for placement around a vulnerable region to be protected such that the at least one compliant enclosure overlies a region adjacent to the vulnerable region but not the vulnerable region itself, the annular shape of the at least one compliant enclosure having an interior area coinciding generally with the vulnerable region to be protected by the pad, the at least one compliant enclosure serving to receive impact energy directed toward the vulnerable region and retransmitting a substantial portion of the impact energy to the adjacent region.

39. The protective pad of claim 38 wherein the shear-thickening material has a critical shear rate between 5 and 30 $s^{-1}$.

40. The protective pad of claim 38 further comprising adhesive means for adhering the at least one compliant enclosure to the body of a subject.

* * * * *